(12) United States Patent
Roberts et al.

(10) Patent No.: US 8,061,208 B2
(45) Date of Patent: Nov. 22, 2011

(54) NON-DESTRUCTIVE PIPE SCANNER

(75) Inventors: Douglas J. Roberts, Willington, CT (US); George R. Rowland, Winsted, CT (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 448 days.

(21) Appl. No.: 12/431,856

(22) Filed: Apr. 29, 2009

(65) Prior Publication Data

US 2010/0275691 A1 Nov. 4, 2010

(51) Int. Cl.
G01N 9/24 (2006.01)
G01N 29/26 (2006.01)
G01N 29/265 (2006.01)

(52) U.S. Cl. .......................................... 73/622; 73/637

(58) Field of Classification Search ................... 73/622, 73/623, 627, 629, 633, 635, 865, 866.5; 356/237.1, 356/240.1
See application file for complete search history.

(56) References Cited

U.S. PATENT DOCUMENTS

| 4,331,034 | A | * | 5/1982 | Takeda et al. ................ 73/637 |
| 4,767,048 | A | | 8/1988 | Kimbrough et al. |
| 6,137,853 | A | * | 10/2000 | Duckering et al. ........... 376/252 |
| 7,398,697 | B2 | * | 7/2008 | Allen et al. ..................... 73/800 |
| 7,852,073 | B2 | * | 12/2010 | Kwun et al. .................. 324/262 |
| 2009/0038398 | A1 | * | 2/2009 | Lavoie et al. ................... 73/637 |
| 2010/0275694 | A1 | * | 11/2010 | Lavoie et al. ................... 73/637 |

FOREIGN PATENT DOCUMENTS

| GB | 2 032 046 A | 4/1980 |
| JP | 2001 305116 A | 10/2001 |
| JP | 2003 270223 A | 9/2003 |
| WO | WO 92/06372 A1 | 4/1992 |
| WO | WO 95/25278 | 9/1995 |

* cited by examiner

Primary Examiner — Lisa Caputo
Assistant Examiner — Jamel Williams

(57) ABSTRACT

A non-destructive examination pipe scanner that employs a main carriage on which a sensor is mounted, a tensioner carriage and an idler carriage. The main carriage and the tensioner carriage are positioned around the pipe at spaced locations and connected on either side by a spring band. The idler carriage is slidably supported by the spring band in between the main carriage and the tensioner carriage. The sensor on the main carriage collects data about a circumferential weld on the pipe as the main carriage drives the tensioner carriage and the idler carriage around the circumference. The tensioner carriage has a variable length connection that adjusts the tension on the spring band to urge the main carriage, idler carriage and tensioner carriage into contact with the surface of the pipe.

18 Claims, 7 Drawing Sheets

NON-DESTRUCTIVE PIPE SCANNER

BACKGROUND OF THE INVENTION

1. Field of the Invention

This invention pertains generally to non-destructive pipe scanners and, more particularly, to pipe scanners that are designed to operate in tight clearance areas.

2. Description of the Related Art

Non-destructive examination of pipes and, more particularly, pipe welds, has a number of applications, few more critical than the inspection of pipe welds in fossil fuel power generating facilities and nuclear power plants. In power plants, the pipes are often arranged close to each other and extend through concrete structures providing little room to maneuver and inspect the pipe seams over their 360° circumference to detect flaws in the welds. A number of the pipes can only be accessed from one axial end through a blind opening and have limited access circumferentially with clearances as little as 1.35 inch (3.4 cm). Furthermore, a number of the pipes vary in diameter from 6.63 inches (16.8 cm) to 24 inches (61 cm) or larger, which makes it difficult to find scanners that can effectively monitor the welds on such piping. Accordingly, there is an increasing demand for highly specialized scanners to deliver sensors such as phased array ultrasonic probes too difficult to access areas.

Thus, it is an object of this invention to provide such a scanner that can inspect the circumferential welds on piping of various diameters that range from 6.63 inches (16.8 cm) to 24 inches (61 cm) or larger, in confines with as little as 1.35 inch (3.4 cm) clearance.

Furthermore, it is an object of this invention to provide such a scanner system that can inspect the pipe welds over the entire 360° circumference of the pipe.

Additionally, it is an object of this invention to provide such a scanner system that is relatively easy to set up and disassemble.

SUMMARY OF THE INVENTION

This invention achieves the foregoing objectives by providing a scanner system for non-destructively scanning the outer circumference of a ferrous or nonferrous tubular object. The scanner system includes a main carriage with wheels at either end and a frame that extends therebetween that supports a non-destructive sensor. The system also includes a tensioner carriage with wheels at either end and a frame with a variable length connection therebetween. Additionally, the system includes one or more idler carriages having wheels at either end and a frame that extends therebetween. A spring band extends from one end of the main carriage around the tubular object and over the idler carriage to one end of the tensioner carriage which is preferably positioned approximately diametrically opposed to the main carriage. Similarly, a spring band extends around the other side of the circumference of the tubular object from the other end of the main carriage over an idler carriage to the other end of the tensioner carriage. The variable length connection on the tensioner carriage is adjusted to place the spring band under tension and urge the main carriage, the tensioner carriage and the idler carriages against the outer circumference of the tubular object. The main carriage can then be driven around the outer circumference of the tubular object so that the on-board non-destructive sensor can scan the weld over the 360° circumference.

Desirably, the main carriage frame has an adjustable frame member that indexes the sensor in an axial direction along a longitudinal dimension of the tubular object. The adjustable frame member may be manually or motor driven and can have an encoder to index the sensor's position. Preferably, at least one wheel of the main carriage has an encoder attached thereto to index the data received from the sensor.

In one embodiment, at least one of the wheels of the main carriage is a drive wheel that is magnetic to gain traction on the tubular object. The drive wheel may be motorized and remotely operated.

In another embodiment, the variable length connection on the tensioner is a scissor mechanism that spans the frame between the forward and rear wheels. Desirably, the scissor mechanism is opened and closed by the rotation of a single screw that preferably cannot be back driven.

In still another embodiment, the frame on the main carriage is arched between the forward and rear wheels. Preferably, the frames on the tensioner carriage and the idler carriages are similarly arched.

BRIEF DESCRIPTION OF THE DRAWINGS

A further understanding of the invention can be gained from the following description of the preferred embodiment when read in conjunction with accompanying drawings in which.

DESCRIPTION OF THE PREFERRED EMBODIMENT

Figure 1:
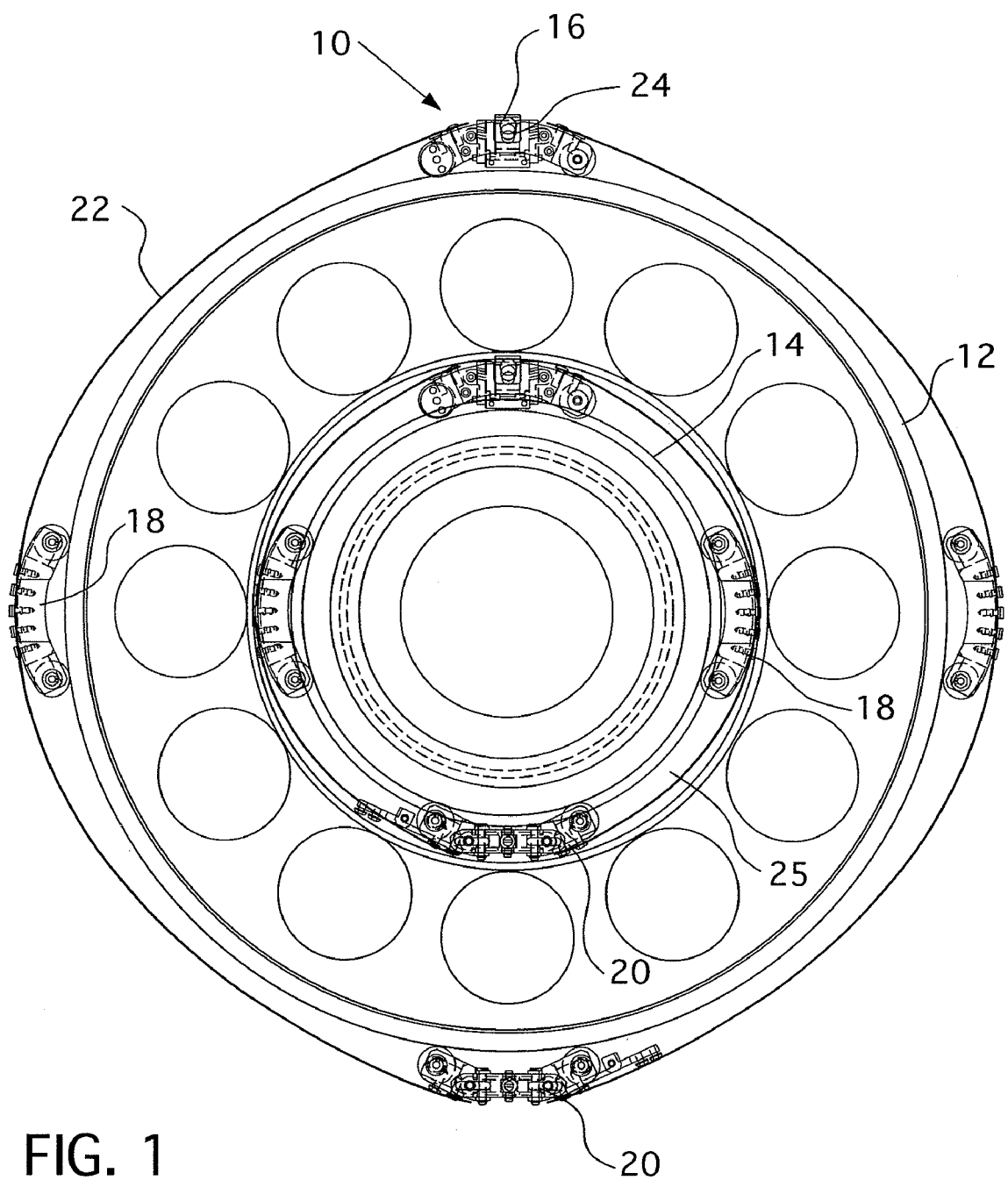
FIG. 1 is a front view of two concentric pipes with a small clearance therebetween in which the scanning system of this invention is mounted with a second system mounted on the outer circumference of the larger pipe.

FIG. 1 is a mock-up of a power plant piping system that shows two concentric pipes 12 and 14 with a narrow clearance 26 therebetween in which the carriages of this invention 16, 18 and 20 are mounted. The carriages 16, 18 and 20 are urged against the outer circumference of the inner pipe 14 by the spring bands 22 that are connected between the main carriage 16 and the tensioner carriage 20 and over the idler carriages 18. The outer circumference of the outer pipe 12 has a similar scanner arrangement to illustrate that the scanner system of this invention can be used to inspect circumferential welds on almost any size pipe and more preferably those having outside diameters which range from 6.63 inches (16.8 cm) to 24 inches (61 cm) or larger. The main carriage 16 includes a flat bearing way 50 that supports the sensor 24. In this embodiment, the sensor 24 extends from the side of the main carriage 16 and can focus a transducer such as an ultrasonic phased array on the weld as the main carriage 16 drives around the outer circumference and over the weld of the pipe or other tubular object. The main carriage 16 also drives the idler carriages 18 and the tensioner carriage 20 through the spring bands 22.

Figure 2:
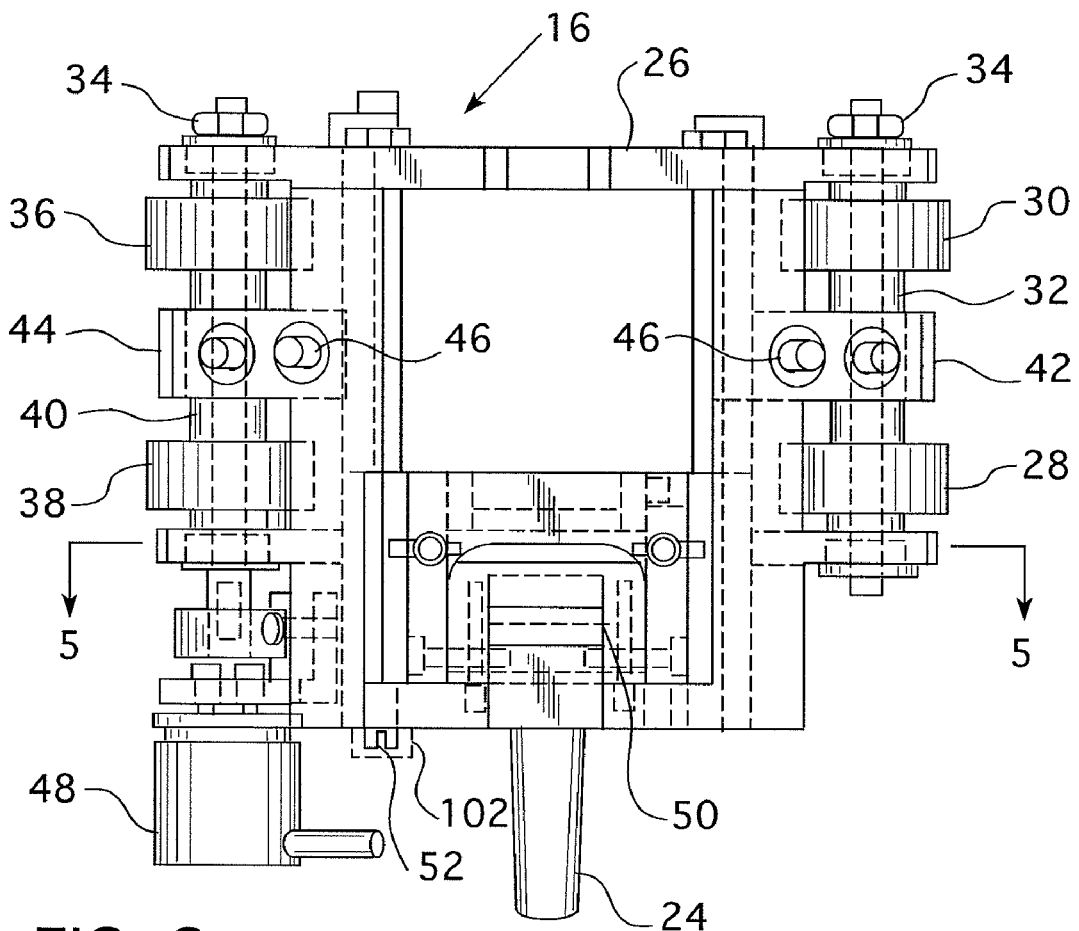
FIG. 2 is a plan view of the main carriage of this invention.
Figure 3:
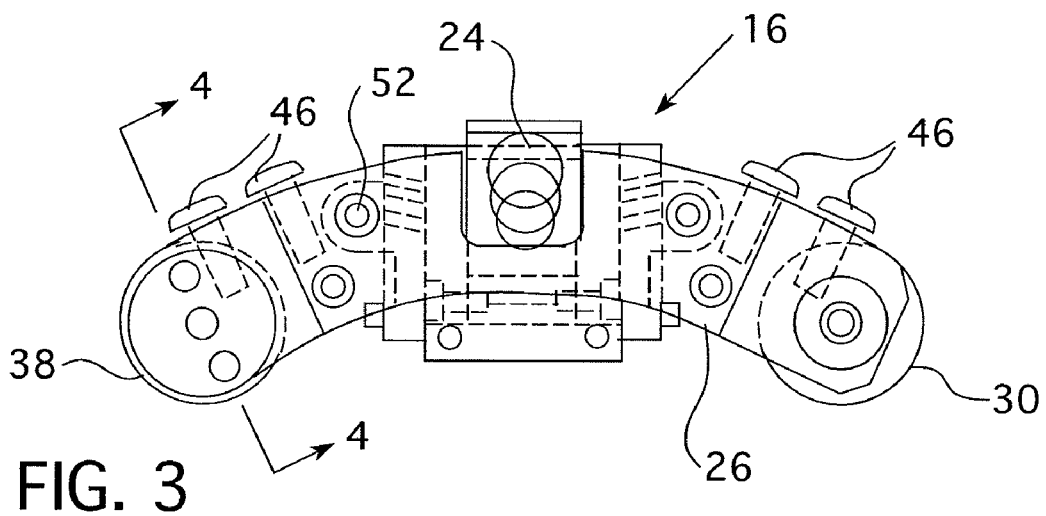
FIG. 3 is a side view of the main carriage shown in FIG. 2.
Figure 4:
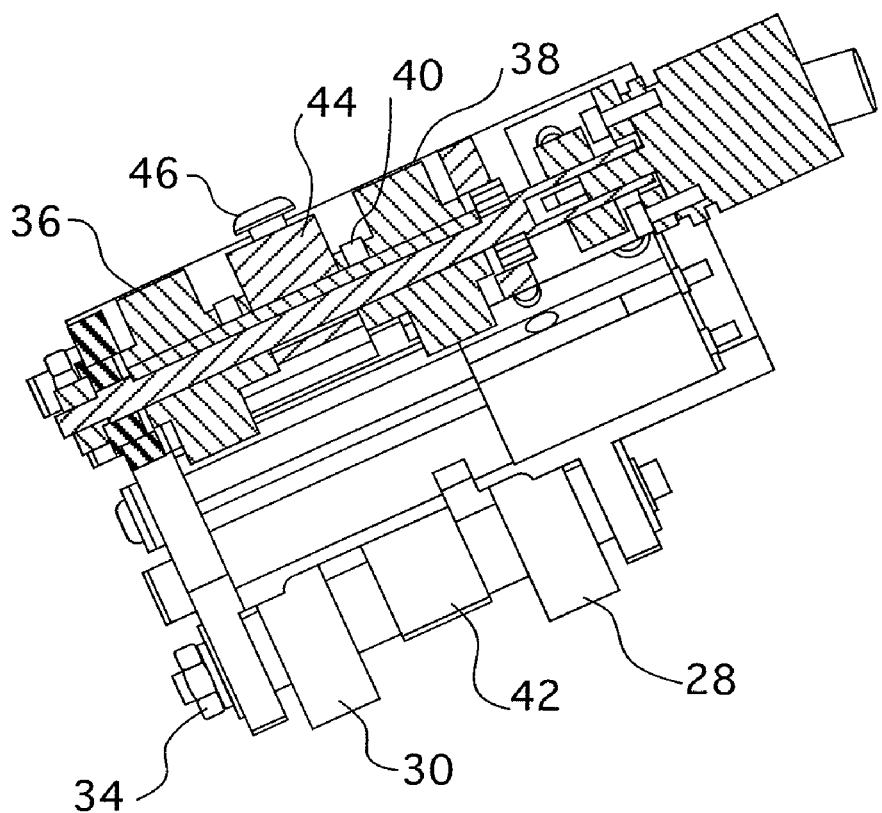
FIG. 4 is a cross-sectional view taken through the lines 4-4 of FIG. 3.
Figure 5:
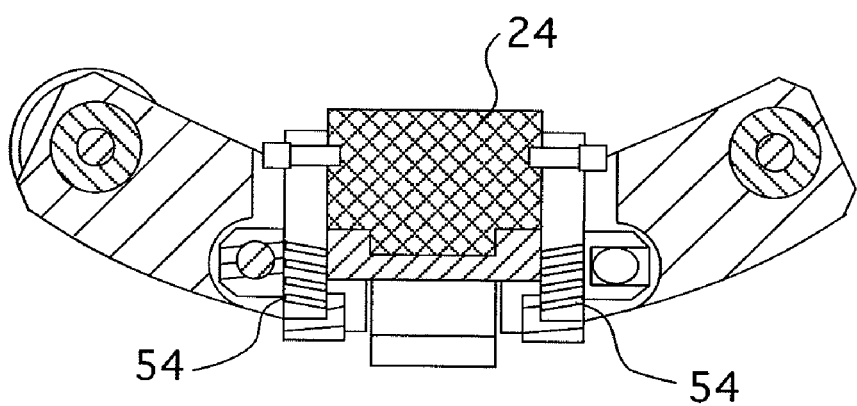
FIG. 5 is a cross-sectional view taken along the lines 5-5 of FIG. 2.

The main carriage 16 is shown in more detail in FIGS. 2-5. FIG. 2 is a plan view of the main carriage 16 and FIG. 3 is a side view of the main carriage shown in FIG. 2. As can best be seen from FIG. 3, the main carriage has an arched frame 26 that supports the axels 32 and 40 (shown in phantom) on which the laterally spaced wheels 28 and 30 and 36 and 38 rotate. The axels are captured and held in place by the axel nuts 34. A front and rear frame extension 40 and 42 extend outwardly from the central frame between the wheels 36 and 38 and 28 and 30. Each frame extension 40 and 42 include two screws 46 that are used to anchor the ends of the corresponding spring band. The front axel 40 has a motor/encoder for driving the wheels 36 and 38 and indexing the position which corresponds to the data received by the sensor 24 so that the location of defects can be identified. The sensor 24 can be an ultrasonic phased array, an eddy current probe, a video camera or any other non-destructive sensor that is capable of surveying the weld. Preferably, the wheels 36 and 38 are magnetized to increase their traction on the pipe surface. The sensor 24 is supported with a lead screw 52 and a flat bearing way 50. The lead screw 52 is used to translate the sensor 24 axially along the pipe for fine tuning or indexing. The lead screw 52 may be operated manually or may be motorized and include an encoder for indexing the sensor's position. The motor/encoder is figuratively shown in FIG. 2 as 102. As can be seen from FIG. 5, which is a cross section taken along the lines 5-5 of FIG. 2, the sensor 24 is biased with the springs 54 against the surface of the pipe to accommodate anomalies in the pipe surface and assure good signal coupling.

Figure 6:
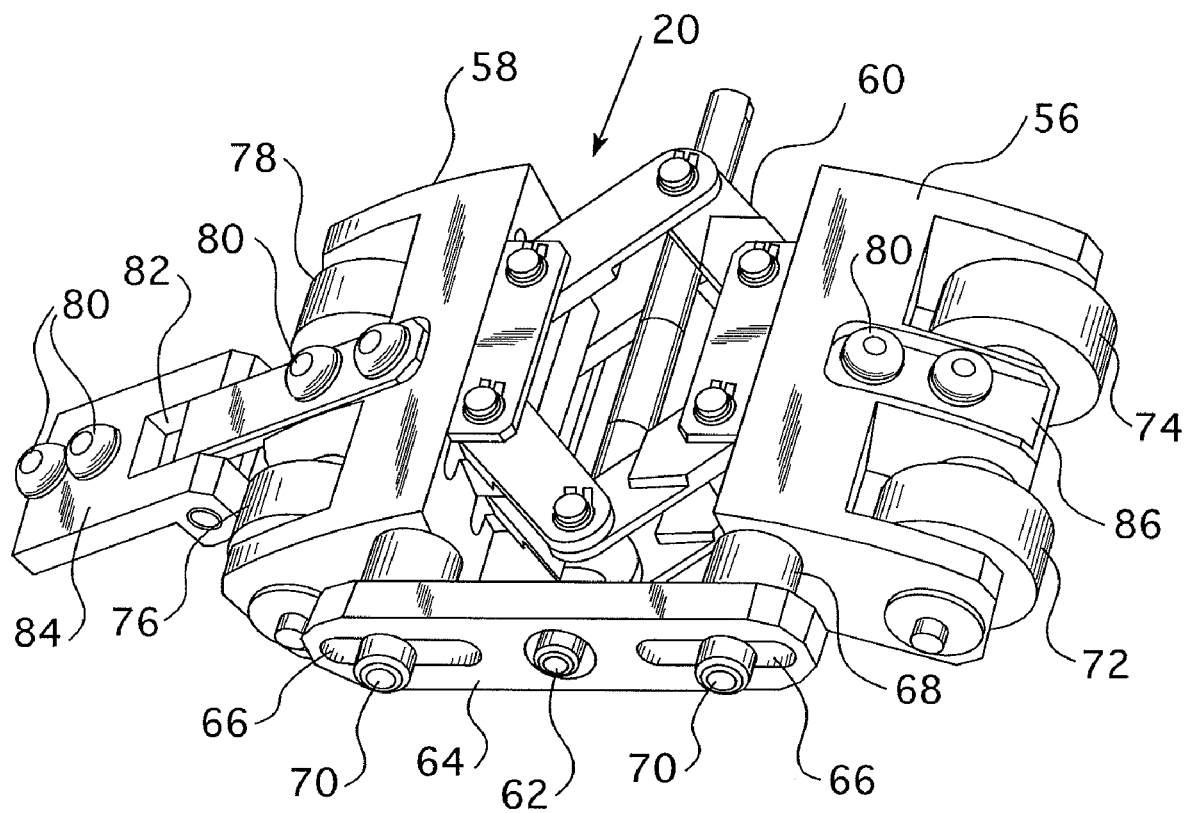
FIG. 6 is perspective view of the tensioner carriage of this invention.

The tensioner carriage is more fully illustrated in FIGS. 6-10. FIG. 6 shows a perspective view of the tensioner carriage 20. As can be seen from FIGS. 6-10, the tensioner carriage 20 has a forward frame portion 56 and a rear frame portion 58 that is connected together with a variable length connection 60. Though a scissor coupling arrangement is shown in FIG. 6 for the variable length connection, it should be appreciated that other mechanical couplings that are adjustable to change the spacing between the front frame section 56 and the rear frame section 58 can be employed. The distance between the front frame portion 56 and the rear frame portion 58 is adjusted with a single screw 62 that is not back drivable, which means that the screw, once adjusted, retains its position during operation. The front frame section 56 is supported laterally with respect to the rear frame section 58 by a frame tie plate 64 that is connected via standoffs 68 to the frame sections 56 and 58 with bolts 70. The spring bands are connected to the front of the tensioner carriage at the attachment plate 86 and to the rear of the carriage at the attachment plate 84 with the screws 80. Alternately, a quick latching operation of the spring band to the rear attachment plate 84 can be achieved by inserting a clevis pin through the spring band and into the clevis slot 82. The adjustment screw 62 allows for infinite adjustment within the operating range of diameters addressed rather than in finite increments.

Figure 7:
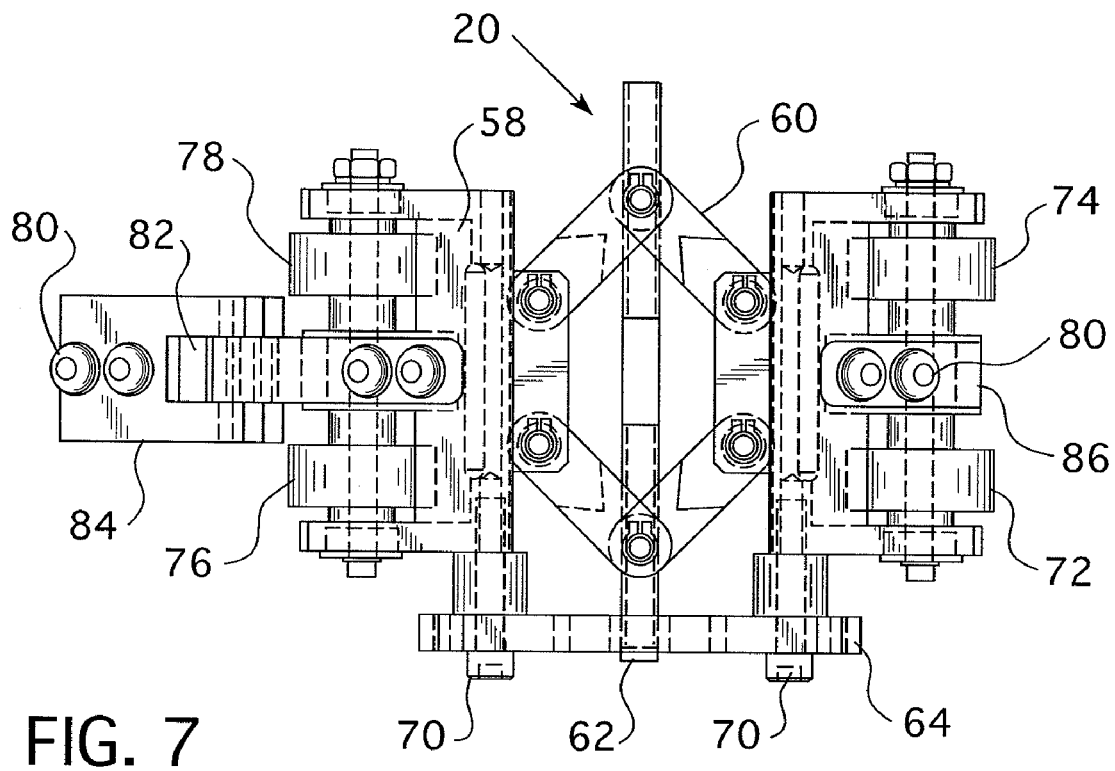
FIG. 7 is a plan view of the tensioner carriage illustrated in FIG. 6.
Figure 8:
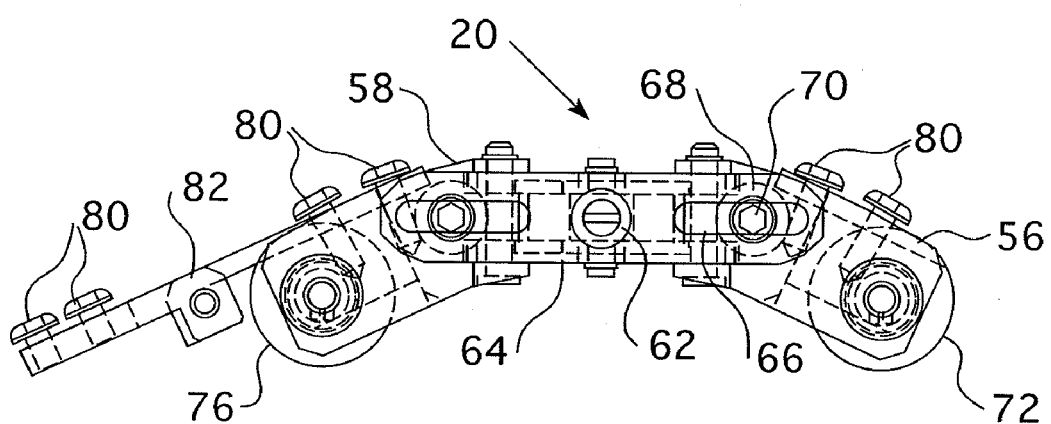
FIG. 8 is a side view of the tensioner carriage illustrated in FIG. 6.
Figure 9:
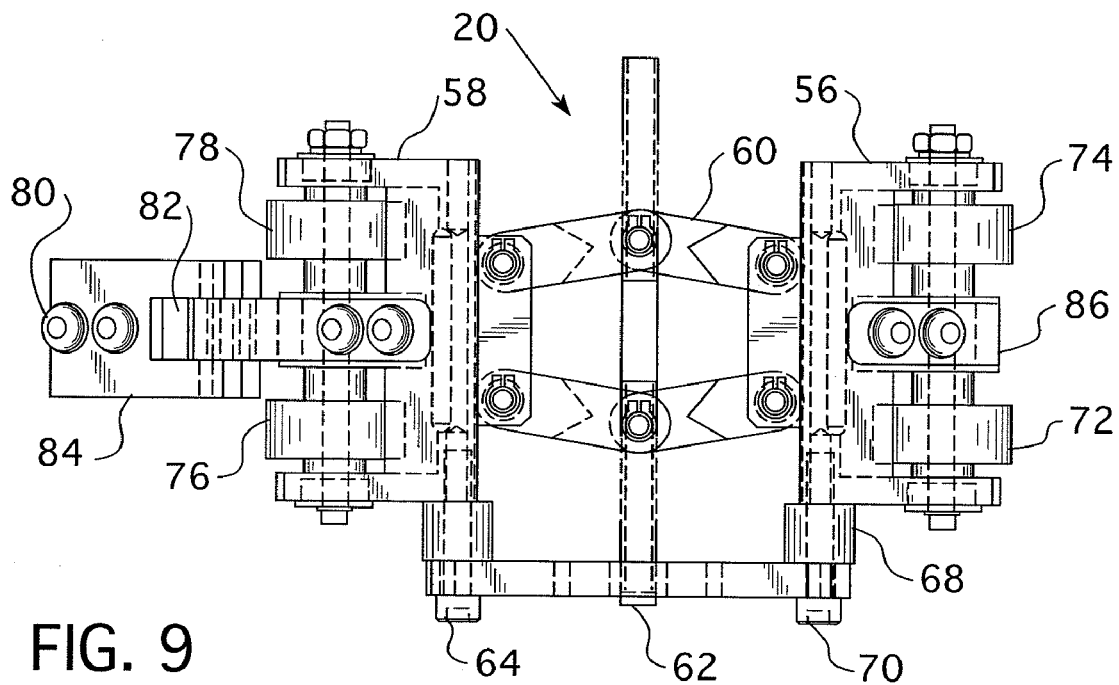
FIG. 9 is a plan view of the tensioner carriage shown in FIG. 6 with the variable length connection substantially completely extended.
Figure 10:
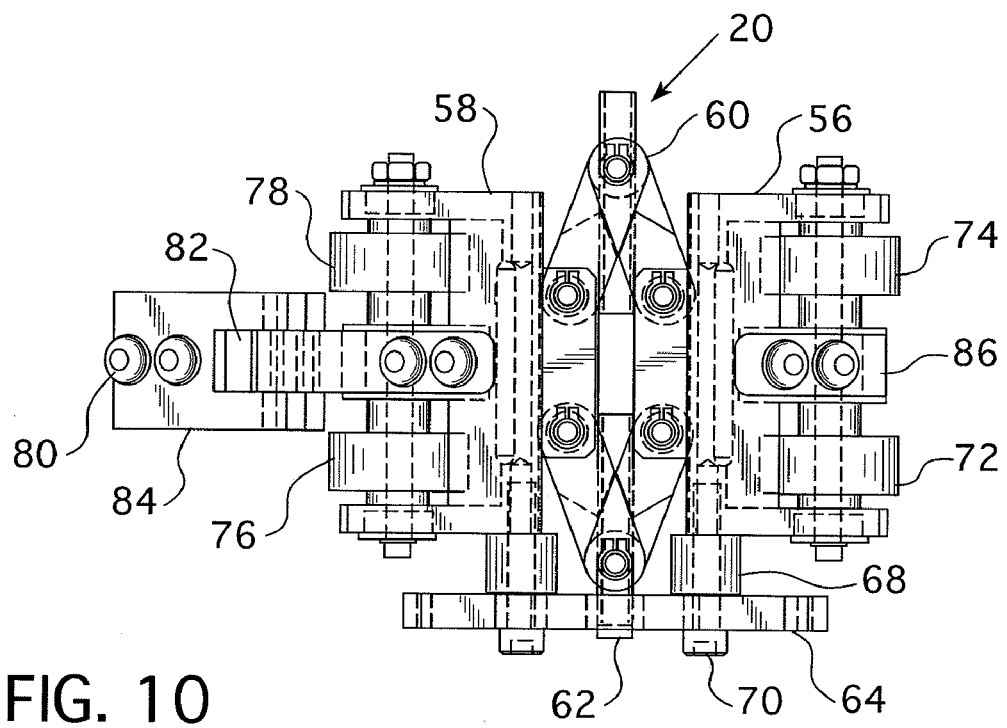
FIG. 10 is a plan view of the tensioner carriage shown in FIG. 6 with the variable length connection substantially retracted.

FIG. 7 is a plan view of the tensioner carriage illustrated in FIG. 6 and FIG. 8 is a side view of the tensioner carriage 20 illustrated in FIG. 7. FIG. 9 is a plan view showing the scissor connection 60 between the front frame section 56 and the rear frame section 58 in the fully extended position. FIG. 10 is a plan view of the tensioner carriage 20 with the variable length connection, e.g., the scissor connection illustrated in FIG. 10, in the fully retracted position. Turning the adjustment screw 62 in a direction that draws the rear frame portion 58 towards the front frame portion 56 adds tension to the spring band and urges the main carriage 16, the idler carriages 18 and the tensioner carriage 20 against the outer surface of the pipe on which the scanning system of this invention is mounted. The arched curvature of the front frame portion 56 and the rear frame portion 58 permits the tensioner carriage 20 to accommodate the curvature of the pipe surface.

Figure 11:
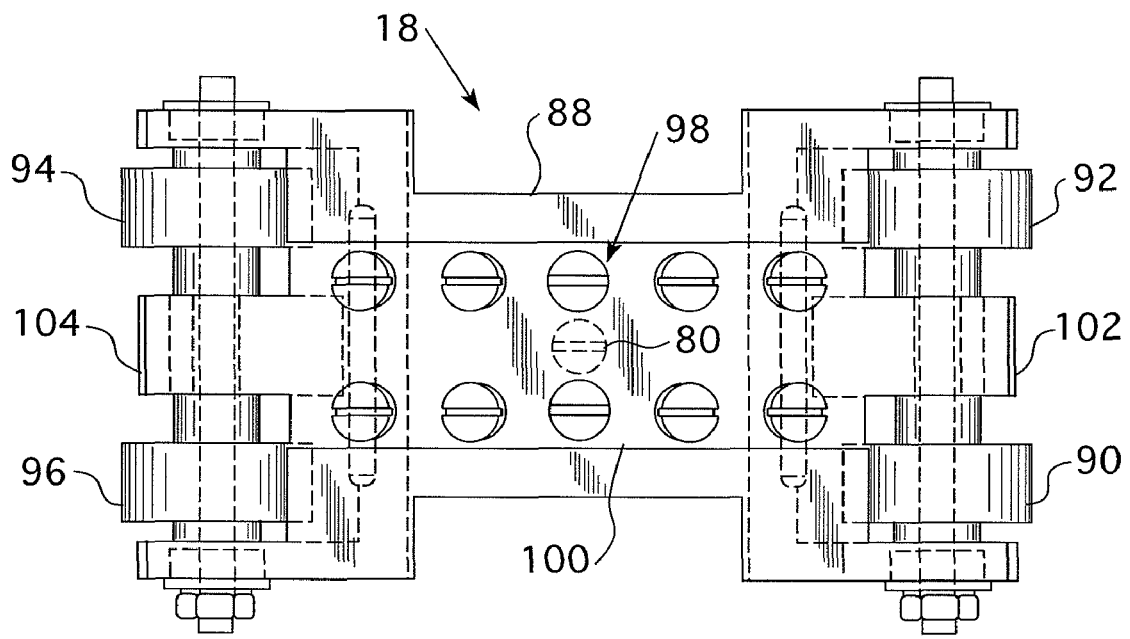
FIG. 11 is a plan view of the idler carriage of this invention.
Figure 12:
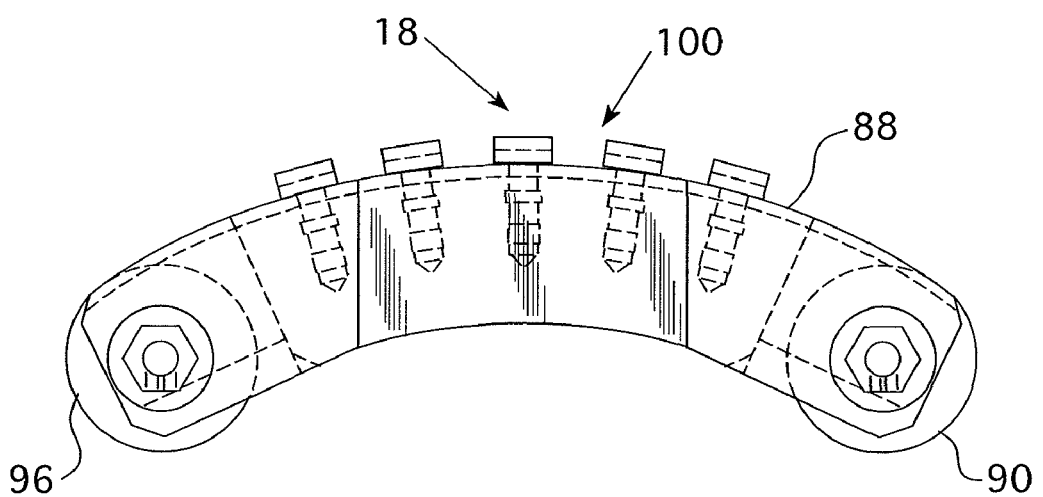
FIG. 12 is side view of the idler carriage illustrated in FIG. 11.

A plan view of the idler carriage 18 is shown in FIG. 11 and a side view of the idler carriage 18 is shown in FIG. 12. The idler carriage 18 has an arched frame 88 similar to that described for the main carriage. The frame 88 supports two laterally spaced wheel pairs 90 and 92 at one end and 94 and 96 at the other end. Two lines of screws 98 and 100 form a guide that slidably receives the spring band under the screw heads between the spring band bearing plates 102 and 104. Thus, while the spring bands are connected to the main carriage 16 and the tensioner carriage 20, the idler carriage 18 is free to slide along the spring band for ease of setup and can be locked in place with, for example, a screw 80 prior to scanning. The idler carriage's function is to raise the spring band above the surface of the pipe to minimize friction that might impede movement of the main carriage 16. One or more idler carriages 18 may be employed depending upon the diameter of the pipe that is being surveyed. The spring bands that hold the carriages together may be constructed out of steel or other suitable material. In the event the drive wheels are magnetized it may be desirable to use a nonmagnetic material for the spring bands. The length of the spring bands are determined by the diameter of the pipe undergoing inspection.

Thus, the invention provides a convenient relatively light weight inspection scanner tool that can fit in spaces having clearances of as little as 1.35 inch (3.4 cm) and can be used on various diameter piping by merely changing the length of the spring bands. The scanner of this invention can be used in blind passages by insertion through the open end and all of the necessary adjustments can be made from that one end. The scanner of this invention is designed to do a full 360° scan with the capacity to index the probe along the axis of the pipe to focus the probe if necessary. The indexing of the probe may be accomplished manually or through the use of a motorized drive.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the breath of the appended claims and any and all equivalents thereof.

What is claimed is:

1. A scanner system for nondestructively scanning the outer circumference of a tubular object comprising:
    a main carriage having wheels at a first and second end of the main carriage and a frame that extends therebetween that supports a nondestructive sensor;
    a tensioner carriage having wheels at a first and second end of the tensioner carriage and a frame with a variable length connection between the first and second end of the tensioner carriage;
    an idler carriage having wheels at a first and second end of the idler carriage and a frame extending therebetween; and a spring band connecting the main carriage to the tensioner carriage and passing over an upper surface of the idler carriage frame between the main carriage and the tensioner carriage in a manner that urges the wheels on the main carriage, the tensioner carriage and the idler carriage against the outer circumference of the tubular object.

2. The scanner system of claim 1 wherein the main carriage frame has an adjustable frame member that indexes the sensor in an axial direction along a longitudinal direction of the tubular object.

3. The scanner system of claim 2 wherein the adjustable frame member is motorized.

4. The scanner system of claim 3 including an encoder for indexing a position of the sensor.

5. The scanner system of claim 1 wherein the main carriage and the tensioner carriage have at least four wheels each, two wheels at either end that are laterally spaced from one another.

6. The scanner system of claim 5 wherein at least one of the wheels on the main carriage at either the first end or the second end has an encoder attached thereto to index the data received from the sensor.

7. The scanner system of claim 5 wherein at least two of the wheels on the main carriage at either the first end or the second end are drive wheels and are magnetic.

8. The scanner system of claim 7 wherein the drive wheels are motorized.

9. The scanner system of claim 1 wherein the variable length connection on the tensioner carriage is a scissor mechanism that is adjustable by rotating a screw.

10. The scanner system of claim 9 wherein the screw cannot be back-driven.

11. The scanner system of claim 1 further including a second idler carriage.

12. The scanner system of claim 1 wherein the spring band extends around the entire circumference of the tubular object between the main carriage and the tensioner carriage.

13. The scanner system of claim 1 wherein retracting the variable length connection between the first and second end of the tensioner carriage tensions the spring band around the tubular object.

14. The scanner system of claim 1 wherein the frame on the main carriage between the wheels on the first and second ends is arched.

15. The scanner system of claim 1 wherein the spring band is slidably connected to the outer surface of the idler carriage so that the spring band can slip over the idler carriage during setup.

16. The scanner system of claim 15 wherein the spring band is locked in place on the idler carriage after setup.

17. The scanner system of claim 1 that has a maximum height above the outer circumference of the tubular object of approximately 1.35 in. (3.35 cm.).

18. The scanner system of claim 1 wherein the spring band is a spring steel band.

* * * * *